United States Patent
Dekel (10) Patent No.: US 7,189,240 B1
(45) Date of Patent: Mar. 13, 2007

(54) METHOD AND APPARATUS FOR SPINAL PROCEDURES

(75) Inventor: Assaf Dekel, Neve-Savyon (IL)

(73) Assignee: Disc-o-Tech Medical Technologies Ltd., Herzlia Pituach (IL)

( * ) Notice: Subject to any disclaimer, the term of this patent is extended or adjusted under 35 U.S.C. 154(b) by 178 days.

(21) Appl. No.: 10/031,450

(22) PCT Filed: Aug. 1, 2000

(86) PCT No.: PCT/IL00/00458

§ 371 (c)(1),
(2), (4) Date: Aug. 6, 2002

(87) PCT Pub. No.: WO01/08571

PCT Pub. Date: Feb. 8, 2001

(30) Foreign Application Priority Data

Aug. 1, 1999 (IL) ...................................... 131197

(51) Int. Cl.
*A61B 17/00* (2006.01)
*A61B 17/56* (2006.01)

(52) U.S. Cl. .......................................... 606/85; 606/84

(58) Field of Classification Search ................... 606/79, 606/84, 85, 80; 451/309, 296, 163, 164, 451/168, 178, 451, 452, 455, 457; 51/138; 407/29.1, 29.11, 29.15
See application file for complete search history.

(56) References Cited

U.S. PATENT DOCUMENTS

| | | | | |
|---|---|---|---|---|
| 2,355,124 A | * | 8/1944 | Testo | 407/29.11 |
| 2,372,553 A | * | 3/1945 | Coddington | 407/29.11 |
| 3,523,348 A | * | 8/1970 | Nilsson | 407/29.11 |
| 5,628,678 A | | 5/1997 | Tridico | |
| 5,713,785 A | * | 2/1998 | Nishio | 451/451 |
| 5,722,977 A | | 3/1998 | Wilhelmy | |
| 5,725,530 A | | 3/1998 | Popken | |
| 5,792,044 A | | 8/1998 | Foley et al. | |
| 5,879,353 A | | 3/1999 | Terry | |
| 6,068,542 A | * | 5/2000 | Hosokai | 451/37 |

FOREIGN PATENT DOCUMENTS

| | | |
|---|---|---|
| DE | 32 09 403 | 9/1983 |
| DE | 40 36 804 | 5/1992 |
| WO | WO 97/09940 | 3/1997 |
| WO | WO 98/29047 | 7/1998 |

* cited by examiner

*Primary Examiner*—Pedro Philogene (57) ABSTRACT

A method of treating spinal stenosis, in which a rasp is brought through a part of a spinal channel and then axially moved so that the rasp removes a stenosis in the spinal channel. Optionally, a shield protects a spinal cord or other sensitive tissues in the spinal channel.

52 Claims, 8 Drawing Sheets

VIEW A

VIEW A

FIG.8A

FIG. 8B

METHOD AND APPARATUS FOR SPINAL PROCEDURES

RELATED APPLICATIONS

The present application is a U.S. national application of PCT/IL00/00458, filed Aug. 1, 2000.

FIELD OF THE INVENTION

The present invention relates to minimally invasive devices and especially to devices for removing bone and/or soft tissue.

BACKGROUND OF THE INVENTION

Degenerative spinal stenosis is a common cause of back and leg pain. A typical causative factor of spinal stenosis is a thickening of bone and/or ligaments into the spinal nerve channel, which thickening applies pressure to the nerves passing through the spinal column.

Figure 1A:
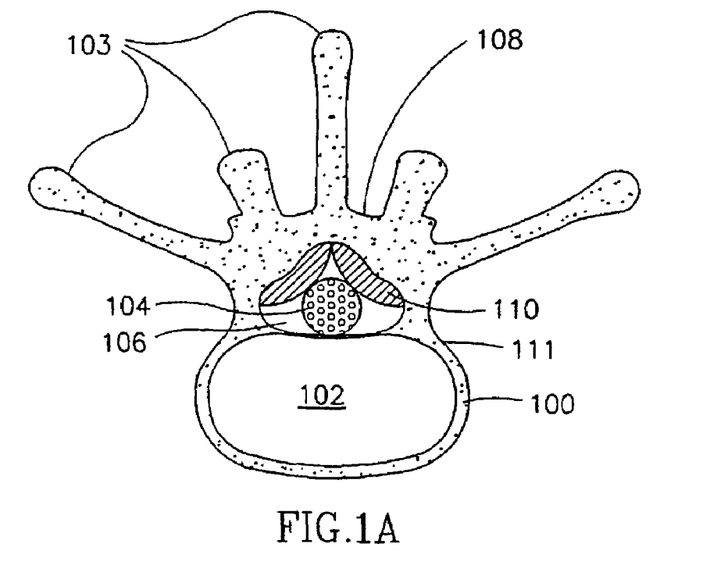
FIGS. 1A and 1B illustrate a vertebra in top and side views respectively, illustrating common types of spinal stenosis.
Figure 1B:
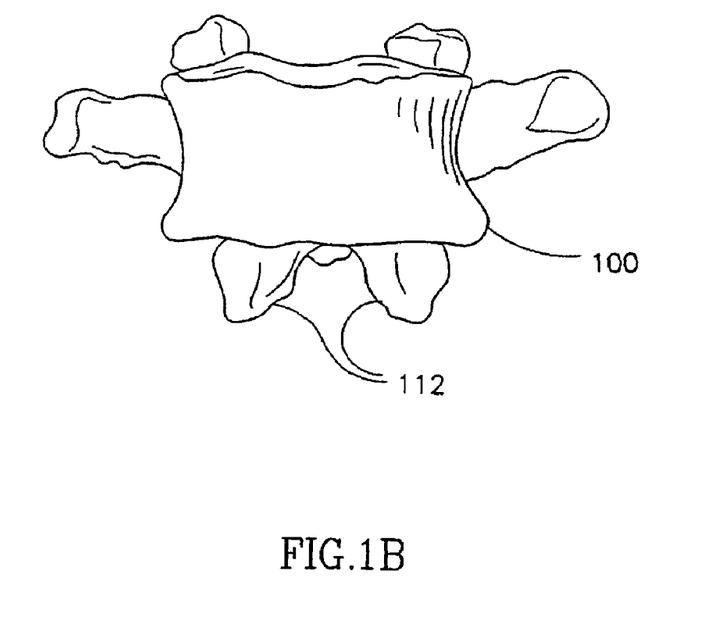

FIGS. 1A and 1B illustrate a vertebra 100 in top and side views respectively, illustrating common types of spinal stenosis. A vertebra 100 comprises a body 102 and processes 103, which surround laminas 108 and pedicles 111. The laminas and the pedicles define a spinal channel 106, in which a spinal cord 104 is disposed. A ligament (yellow ligament, ligamentum flavum) 110 separates spinal cord 104 from the lamina 108.

FIG. 1B shows a side view illustrating a pair of inferior articular processes 112.

Typical causes of spinal stenosis include:
(a) thickening and calcification of ligament 110;
(b) thickening of lamina 108; and
(c) hypertrophy of the joint between two vertebra and especially the inferior articular processes 112, for example due to degenerative changes.

Most often, spinal stenosis is caused by a combination of (a) and (c) above.

One known surgical procedure for treating spinal stenosis is lumbar laminectomy in which the bony outer layer of the spinal column is removed, to allow room for cord 104. In a variation of this procedure, windowed laminectomy, only plugs of the bone are removed, for example at articular processes 112, thereby reducing trauma to the spine and associated tissues.

One problem with the full laminectomy methods is that the spine loses stability so the spine usually needs to be fused. Another problem is that laminectomy is a major surgery, often not suitable for the elderly, who, as a group, are more likely to suffer from spinal stenosis than other age groups. In addition, laminectomy has an associated overall surgical mortality rate of about a 1%.

German patent publication DE 40 36 804 A1, the disclosure of which is incorporated herein by reference describes a device for removing portions of the spine, apparently for correcting spinal stenosis, for example stenosis caused by spondylolytic damage.

SUMMARY OF THE INVENTION

One object of some exemplary embodiments of the invention is to enlarge a spinal lumen using minimally invasive techniques, especially for treating spinal stenosis.

One aspect of some exemplary embodiments of the invention relates to a method of removing axial extends of spinal bone, from inside the spinal channel, especially for relieving spinal stenosis. In an exemplary embodiment of the invention, a bone removing device is inserted into the channel, between a spinal cord and a protrusion and the device is activated to remove the protrusion.

An aspect of some exemplary embodiments of the invention relates to a method of spinal surgery in which portions of the spine, not adjacent to joints thereof are removed using minimally invasive techniques, such as using an endoscope, which techniques do not require a large incision in the back. Optionally, the bone is removed from inside the spinal channel. Alternatively, the bone is removed in plugs, form outside the channel.

An aspect of some exemplary embodiments of the invention relates to entering the spinal column at one point thereof, traveling along the spinal column and exiting at a second point along the spinal column. Optionally, a bone removing device is provided along this path to remove portions of bone and/or other tissues which cause stenosis of the spinal column. In some cases, the bone removing device is provided along a secondary path, such as the channel of a branching nerve, rather than the main channel of the spine. Thus, stenosis of a branching nerve may also be directly treated.

An aspect of some exemplary embodiments of the invention relates to such a path comprising more than one vertebrae, for example, two, three, four, five, six, seven or even more. In an exemplary embodiment of the invention, stenosis along all the vertebrae are treated simultaneously. Alternatively, only fewer than all the vertebra, such as only one, are treated at a time.

An aspect of some exemplary embodiments of the invention relates to moving a device axially along the spinal column and inside the spinal column. Possibly, the device exits the spinal column and then the body, using only forward motion. In an exemplary embodiment of the invention, the device is a leader which pulls behind it a rasp. Alternatively or additionally, the device is a side or forward looking endoscope or ultrasonic imager, used to diagnose the condition of the spinal column and/or of the spinal nerve.

An aspect of some exemplary embodiments of the invention relates to removing bone tissue, especially in the spinal column, by axial rasping, in which an axially moving bone rasping device removes the bone. This removal is instead of or in addition to rotational rasping by a rotating bone rasping device. Alternatively, only rotational rasping is provided, in which the axis of rotation is optionally aligned with the axis of the spine. In an exemplary embodiment of the invention, the rasping motion (rotational and/or axial) is unidirectional. Alternatively, the rasping motion is reciprocating.

A related aspect of some exemplary embodiments of the invention is an axially elongated rasp, which may be flexible, for removing bone and/or other tissue from within a spinal column.

An aspect of some exemplary embodiments of the invention relates to a device for inserting a rasp along a spinal column. In an exemplary embodiment of the invention, the device includes a feeder for feeding a rasp into an entry hole and through the spinal column and a take-up for taking up the rasp from the spinal column, at an exit hole. Possibly, the rasp rotates. Possibly, the rasp exhibits spiral motion along its length, possibly assisting in removing debris from the spinal column.

An aspect of some exemplary embodiments of the invention relates to protective mechanisms for protecting portions of the spine from undesired action of the rasp. In an exemplary embodiment of the invention, a protective layer or device is provided between the rasp and the spinal cord (or its dura), so that the rasp does not come in contact with the spinal cord or even the dura. This layer optionally does not move with the rasp. Such a layer may also be used for a rotating rasp. Alternatively to the layer not moving, it may move with the rasp or even be integral with it. For example, the back of the rasp is made smooth so that any contact between it and the dura does not stress or otherwise damage the dura or the underlying spinal cord. Alternatively or additionally, a shield is provided between the rasp and the spinal column at points where limited or no rasping action is desired. An example of such a location is surrounding the entry point and/or exit point of the rasp-path in the spinal column. Another example of locating a shield in accordance with an exemplary embodiment of the invention is to provide a shield only at certain axial and/or trans-axial locations along the path in the spinal column, to support spatially selective removal of bone and/or ligaments.

An aspect of some exemplary embodiments of the invention relates to a method of treating the spine in which a device for treating the spine is temporarily connected to two non-adjacent vertebrae. In an exemplary embodiment of the invention, attachment of the device to the vertebra is utilized to guide the motion of a section of the device through the spinal channel.

An aspect of some exemplary embodiments of the invention relates to removing portions of the spine which are located along the spinal channel and near a center of a vertebra, without damaging the vertebra outside the spinal channel. In an exemplary embodiment of the invention, a rasp is provided inside the spinal channel, from the spaces between the vertebra and this rasp removes portions of the vertebra, only on the inside of the channel.

There is thus provided in accordance with an exemplary embodiment of the invention, a method of modifying a spine, comprising:

guiding a bone removal device to the spine; and removing axial extents of said spine using said device. Optionally, said device comprises an axially moving rasp.

There is also provided in accordance with an exemplary embodiment of the invention, a method of modifying a spine, comprising:

guiding a bone removal device to the spine, through a tube lumen; and removing portions of said spine using said device.

There is also provided in accordance with an exemplary embodiment of the invention, a method of operating on a spine, comprising:

inserting a device into a spinal channel of said spine; and advancing said device along said channel, for the length of at least two vertebra.

There is also provided in accordance with an exemplary embodiment of the invention, a method of inserting an elongate, flexible device into a spine, comprising:

guiding a tip of the device between two vertebra into a spinal channel of said spine;

guiding said tip along said spine; and existing said tip from said spine and from said body.

There is also provided in accordance with an exemplary embodiment of the invention, apparatus for removing bone, comprising:

a handle;

a first extension attached to said handle;

a second extension attached to said handle; and a flexible rasp extending between a tip of said first extension and a tip of said second extension. Optionally, said rasp moves axially between said tips. Optionally, the apparatus comprises a pick-up reel for advancing said rasp between said tips.

In an exemplary embodiment of the invention, the apparatus comprises a shield adjacent said rasp, to prevent contact of said rasp with tissue at at least some locations along said rasp. Optionally, said rasp has two faces, and wherein said shield protects tissue from one face of said rasp. Alternatively or additionally, said rasp is positioned between said shield and said handle, such that said rasp has an at least partially unshielded active face towards said handle. Alternatively or additionally, the relative positions of the rasp and shield with respect to said handle are changeable by rotation of at least one of the rasp and the shield around an axis connecting said tips.

In an exemplary embodiment of the invention, said rasp has two narrow sides and wherein said shield protects tissue from the sides of said rasp. Alternatively or additionally, said shield is fixed relative to said tips. Alternatively or additionally, said shield is adapted to move axially with said rasp. Optionally, said shield comprises a smooth backing on said rasp.

In an exemplary embodiment of the invention, said shield comprises a channel within which said rasp is positioned. Optionally, said shield cooperates with said rasp to accumulate tissue removed by said rasp between said rasp and said shield.

In an exemplary embodiment of the invention, the apparatus comprises at least one resting point at at least one of said extensions, which resting point is adapted to engage a vertebra. Alternatively or additionally, said rasp has a transaxial width narrow enough to fit inside a vertebral channel of a adult human. Alternatively or additionally, said rasp is less than 7 mm wide in a transaxial direction. Alternatively or additionally, said rasp is less than 5 mm wide. Alternatively or additionally, said rasp is less than 3 mm wide. Alternatively or additionally, said rasp is less than 2 mm wide. Alternatively or additionally, said rasp is thinner than 1 mm. Alternatively or additionally, said rasp is thinner than 0.5 mm. Alternatively or additionally, said rasp is thinner than 0.3 mm. Alternatively or additionally, said rasp is thinner than 0.1 mm.

In an exemplary embodiment of the invention, said rasp is adapted to remove vertebral bone. Alternatively or additionally, said rasp is adapted to remove calcifications. Alternatively or additionally, said rasp is adapted to remove ligament tissue. Alternatively or additionally, said rasp is formed of metal. Alternatively, said rasp is formed of a bioabsorbable material.

In an exemplary embodiment of the invention, a plurality of rasp elements are defined on said rasp. Optionally, said elements are defined by etching. Alternatively or additionally, said elements are defined by punching.

In an exemplary embodiment of the invention, a plurality of rasp elements are attached to said rasp.

In an alternative embodiment of the invention, said rasp comprises a cable. Alternatively, said rasp comprises a chain.

In an exemplary embodiment of the invention, said rasp elements are adapted to guide removed tissue away from the tissue on which the rasp is working.

In an exemplary embodiment of the invention, said rasp elements are adapted to retain removed tissue.

In an exemplary embodiment of the invention, the apparatus comprises a source of cleaning fluid, adjacent said rasp. Alternatively or additionally, the apparatus comprises a source of vacuum, adjacent said rasp.

In an exemplary embodiment of the invention, said rasp has a total length selected to be substantially sufficient for a spinal stenosis removal procedure. Alternatively or additionally, said rasp has a total length of between 0.5 and 4 meters. Alternatively or additionally, said rasp has a total length of between 1 and 3 meters.

In an exemplary embodiment of the invention, said rasp has an active length defined by a distance between said tips. Alternatively or additionally, said active length is adjustable by adjusting a distance between said tips. Alternatively or additionally, said active length is sufficient to span between one and ten vertebra of a adult human. Alternatively or additionally, said active length is sufficient to span between two and eight vertebra of a adult human. Alternatively or additionally, said active length is sufficient to span between three and four vertebra of a adult human.

In an exemplary embodiment of the invention, said extensions are sufficiently long to extend from a body surface to a spinal channel of a adult human. Alternatively or additionally, the apparatus comprises a rasp advancer for advancing said rasp in a single direction. Alternatively or additionally, the apparatus comprises a rasp advancer for reciprocating said rasp.

In an exemplary embodiment of the invention, said apparatus comprises at least two parts, separable such that said first and said second extensions are in separate parts during a normal use of said apparatus. Alternatively or additionally, the apparatus comprises means for affixing said apparatus to a vertebra. Alternatively or additionally, the apparatus comprises a spring for setting a tension in said rasp . Alternatively or additionally, the apparatus comprises a spring for setting a surface pressure of said rasp against a working surface. Alternatively or additionally, the apparatus comprises a gauge for measuring a tension in said rasp. Alternatively or additionally, the apparatus comprises a leader attached to one end of said rasp, which leader is adapted for inserting through a spinal channel.

There is also provided in accordance with an exemplary embodiment of the invention, apparatus for spinal stenosis treatment, comprising:

means for guiding a rasp through a part of a spinal channel defined by at least one vertebra;

means for holding said rasp on either side of said part of a channel and outside a human or animal body including said vertebra; and means for moving said rasp to remove a spinal stenosis in said spinal channel.

BRIEF DESCRIPTION OF THE DRAWINGS

Some embodiments of the present invention will now be described with reference to the following description of exemplary embodiments thereof in conjunction with the figures, wherein identical structures, elements or parts which appear in more than one figure are labeled with a similar numeral in all the figures in which they appear, in which.

DETAILED DESCRIPTION OF EXEMPLARY EMBODIMENTS

Figure 2:
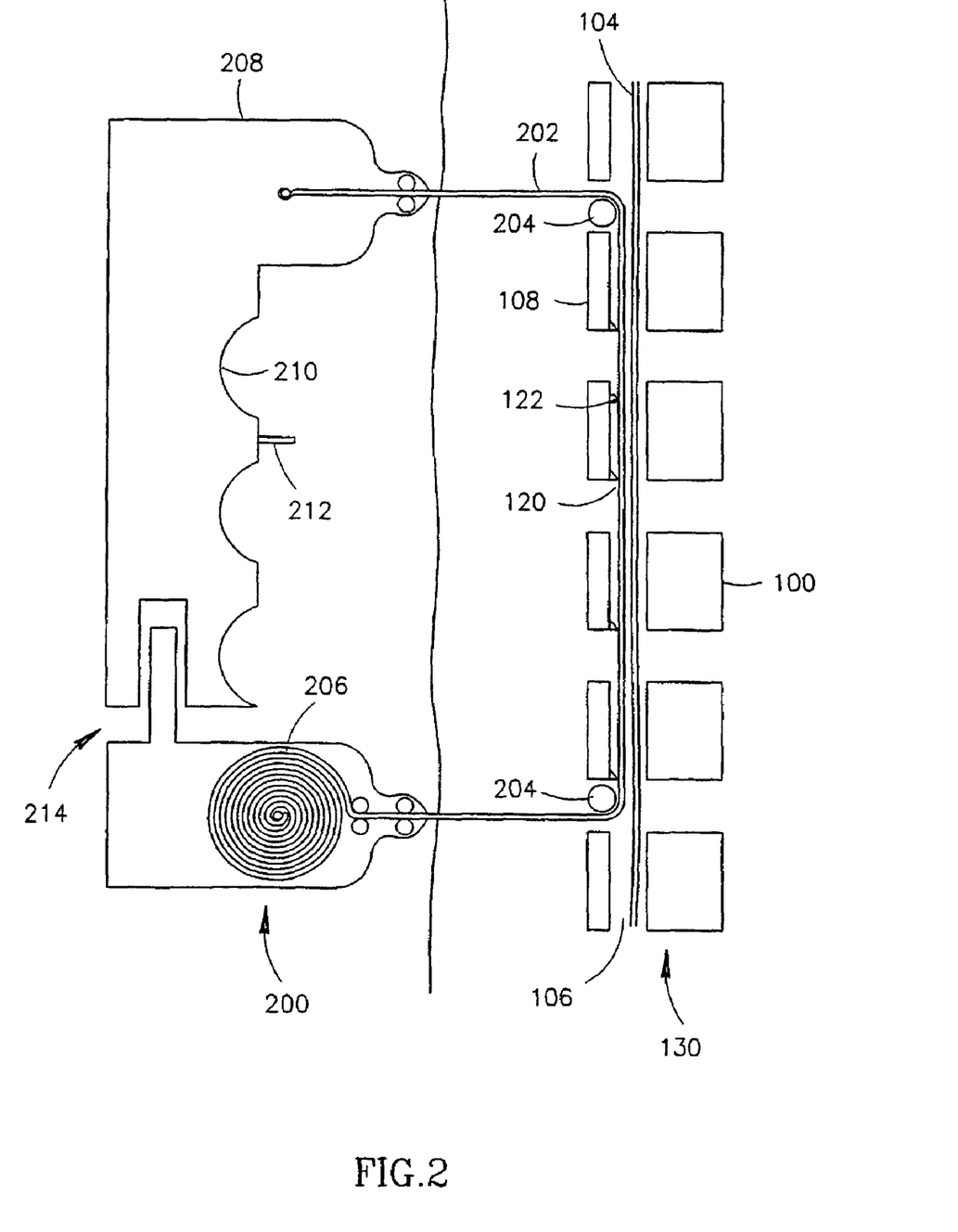
FIG. 2 is a schematic side illustration of the deployment of a bone removal device in a spine, in accordance with an exemplary embodiment of the invention.

FIG. 2 is a schematic side illustration of the deployment of a bone removal device 200 in a spine 130, in accordance with an exemplary embodiment of the invention. Device 200, in an exemplary embodiment of the invention, comprises generally of a rasp provider 206, a rasp take-up 208 coupled to it via a connector 214 and a rasp 202 which passes from the provider 206, through spine 130 and to take-up 208. Optionally, device 200 includes a handle 210 and at least one control 212, for example an on/off switch. A pair of rasp elbows 204 are optionally provided to guide rasp 202 at a proper angle through spinal channel 106. In FIG. 2, two types of stenosis are shown, articulated processes stenosis 120 (several shown) and laminar stenosis 122 (one shown). In an exemplary embodiment of the invention, one or both types of stenosis causing protrusions are removed, possibly selectively, as described below, thereby increasing the cross-section of the spinal channel.

In an exemplary embodiment of the invention, rasp 202 is guided by elbows 204 so that its cutting surface (see below FIGS. 4A–4E) is parallel to the portions to be removed. In some cases this may require rotating the rasp around the axis of the spine. In an exemplary embodiment of the invention, such rotation is provided by elbows 204, for example by the elbows rotating or having two or more channels for guiding the rasp. When the rasp is inserted into the body, the angle of bend at the elbow is optionally 90°, so that the rasp is parallel to the spine axis. In some cases, it may be desirable to have a different angle, for example between 70° and 90° or between 90° and 110°. Alternatively or additionally, a two step bend may be provided, for example to better match the anatomy.

Device 200 may be employed in many parts of the spine, including the lumbar region and the cervical region.

Figure 3A:
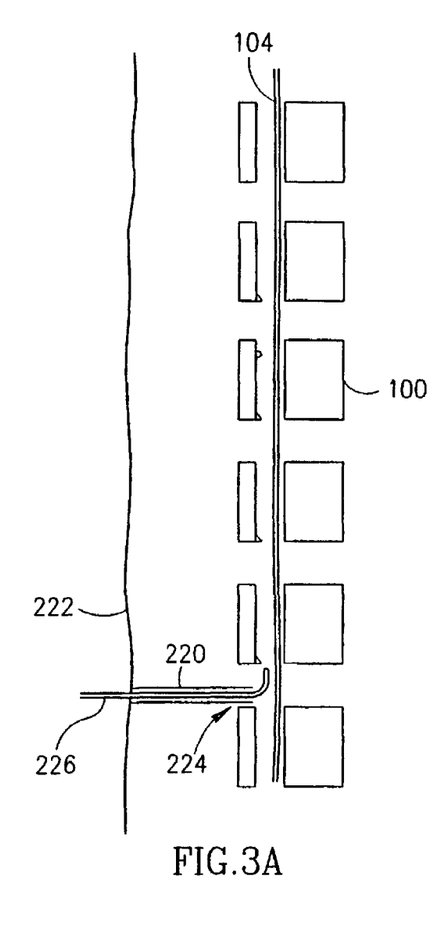
FIGS. 3A–3C schematically illustrate stages in the deployment of the device of FIG. 2, in accordance with an exemplary embodiment of the invention.
Figure 3B:
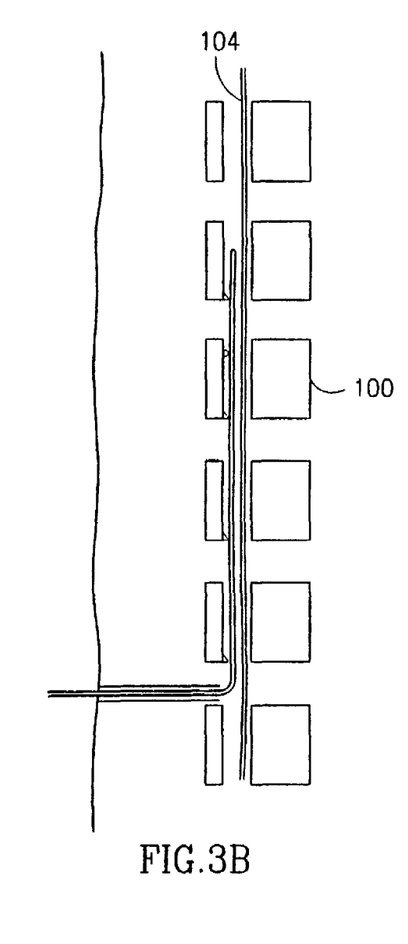
Figure 3C:
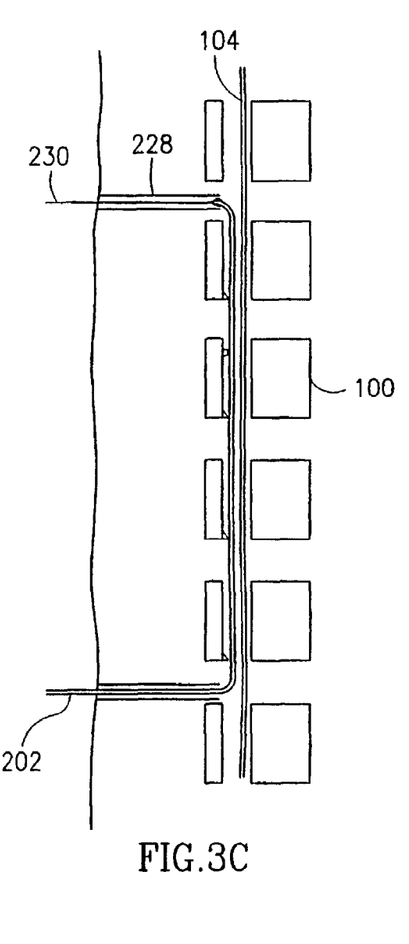

FIGS. 3A–3C schematically illustrate stages in the deployment of device 200 of FIG. 2, in accordance with an exemplary embodiment of the invention. In a typical procedure, rasp 202 is guided through the spinal channel 106 and then the take-up 208 and provider 206 are connected. Alternatively, take-up 208 and provider 206 are interconnected during the insertion process or pre-connected (or even a single element to begin with) and once rasp 202 is guided through the body it is inserted into take-up 208. FIGS. 3A–3C illustrate one family of possible methods of guiding rasp 202 through channel 106, in other embodiments of the invention, other methods may be practiced. Although entry and exit between vertebrae is shown, in some cases entry and/or exit through a vertebra may be desirable. Further, in some cases the entry and exit are at the midline of the spine. However, in others the entry and/or exit may be off the midline, possible on opposite sides of the midline.

In FIG. 3A, an incision 220 is formed between a skin 222 and an entry area 224 into the spinal channel. A guide wire or a soft catheter 226 is optionally inserted through the incision and into the spinal channel. In some embodiments of the invention, incision 220 is formed using an endoscope or a rigid hollow tube, such as a cannula or a needle. In others, a standard surgical incision is formed.

In FIG. 3B catheter 226 is advanced along-side the spinal cord, inside the spinal channel.

In FIG. 3C, catheter 226 is removed from the spinal channel, for example, as shown using a grasping tool 230 inserted through a second incision 228. Alternatively or additionally, a second endoscope (with a grasping tool) is used to remove the catheter. In an exemplary embodiment of the invention, the tip of catheter 226 is marked to make it easier to locate in the incision 228. Such marking can include color, radiant marking such as a blinking LED or an RF transponder, vibration, a unique shape such as a hard sphere, or other means, for example means known in the art for locating objects in a body and especially in a surgical incision. Alternatively or additionally, an automatic guidance system may be used, for example with the catheter tip being magnetic or attracted to a magnet or using a position sensor mounted at the tip of the catheter. Alternatively or additionally, a stylet is inserted into catheter 226, to aid in pushing it out of the body. Alternatively or additionally, catheter 226 includes a lumen for a retractable sharp tip, which can be extended to cut the tissue ahead of the catheter. Alternatively or additionally, an extendible eye (or other anchor) is provided, for the grasping tool (see below) to grasp. Possible, the leading edge of the anchor is sharp, to perform cutting.

Once catheter 226 exists through incision 228, it may be pulled to thread an attached rasp 202 through the spinal column.

Once the use of rasp 202 is completed, the rasp may be pulled forward or backwards so that it leaves the body. Alternatively, the rasp may be cut at any point along its length. Possibly a catheter is inserted into the body in order to cut the rasp.

In some cases, it may be useful to enter at a lower part of the spine and exit at a higher part of the spine. In others, entry is at a higher part and exit at a lower part of the spine. Although a soft catheter is described, in some cases a steerable catheter may be desirable. Alternatively or additionally, the catheter may include an imaging and/or other type of sensor to aid in avoiding damage to the spinal cord while advancing the catheter. Alternatively or additionally, the catheter may have non-uniform bend resistance, for example to prevent twisting of the catheter or bending of the catheter out of the plane of the rasp. In a particular example, the catheter has a rectangular profile. Alternatively or additionally, stiffening spines (or other structural elements) are provided along one transaxial dimension of the catheter and not along the other. Alternatively or additionally, selective weakening of the catheter structure is performed along the other transaxial dimension.

In an exemplary embodiment of the invention, the motion of rasp 202 is one directional. Alternatively, the motion of rasp 202 is reciprocating. Possibly, the motion is a combination of a slow advance in one direction and reciprocating motion, thus, "used" rasp portions are slowly cycled out of the spine. In reciprocating motion, the rasp can remove bone tissue on both the forward and the backwards stroke. Alternatively or additionally, only one of the strokes removes bone, for example only the forward stroke or the backward stroke. Possibly, the other (or both) the strokes remove soft tissue, either exclusively or additionally to removing bone. This selectivity maybe achieved, for example by the design of the rasp or by alternating slow and fast motion of the rasp for the different stroke directions. In another example, the tension in the rasp (for a flexible rasp) is reduced for one of the stroke directions, to reduce the rasping effect of rasp 202.

Alternatively or additionally to linear motion of the rasp, in some exemplary embodiments of the invention the rasp rotates around its axis. If the rasp is twisted or suitably ribbed, this can have the effect of a spiral motion. Alternatively or additionally, a spiral motion is effected by a simultaneous advance and rotation of the rasp.

In an exemplary embodiment of the invention, the motion of the rasp is continuous, except where stopped by the user (or by a safety mechanism). Alternatively, pulsed motion is used, one example of pulsed motion is to activate the rasp for a fixed number of cycles, pre activation pulse. Another example of pulsed motion is to move the rasp a fixed distance for each activation pulse.

In an exemplary embodiment of the invention, the spine is bent and/or straightened so that the rasp is in proper contact with the protrusions to be removed. One method of bending the spine is to place pillows under a stomach of a patient, possibly using feedback from an X-ray image. A set of suitable pillows may be provided in a kit from with the rasp. Possibly, inflatable bladders are used for the pillows. Possibly the bladders are single use bladders. Another method of bending the spine is to apply traction to the spine, while the patient is in horizontal or vertical orientation. Alternatively or additionally, other methods and devices, such as known in the art, may be used to bend the spine.

In one exemplary embodiment of the invention, all the stenosis locations along the rasp are treated simultaneously. Alternatively or additionally, after a first rasping step, only those locations which are not thinned enough by the rasping are rasped again, in series or in parallel. This may require modifying the rasp or moving pillows.

Figure 4A:
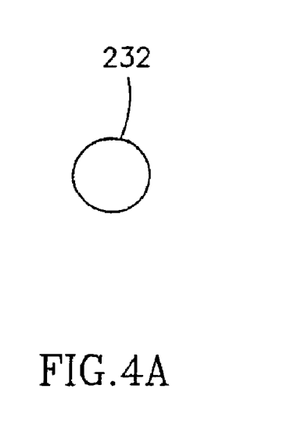
FIGS. 4A–4E illustrate several profiles of a rasp, in accordance with exemplary embodiments of the invention.
Figure 4B:
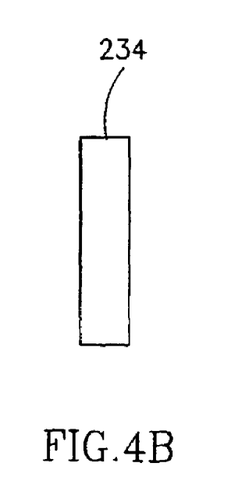

FIGS. 4A–4E illustrates several profiles of a rasp, in accordance with exemplary embodiments of the invention. FIG. 4A shows an exemplary, rounded, profile 232. FIG. 4B shows an exemplary, rectangular, profile 234. Other profiles may be used as well, for example a convex or a concave arc. The profile of FIG. 4A, for example, may be moved axially and/or rotated around its axis for removing bone tissue, depending on the type of device used.

The profile may be constant along the rasp. Alternatively the profile may vary along the rasp. In one example, the profile remains relatively constant for long stretches of the rasp and then changes, for example, to support a two step rasping procedure—first rough rasping and then fine rasping or first a rasp adapted to remove ligament and then a rasp adapted to remove bone. In another example the profile varies locally, for example alternating fine and rough rasping elements, to achieve a particular effect of the rasp on the bone. In another example, the profile varies so as to form grooves in the rasp for the debris of the rasping to travel along. Optionally, such grooves lead the debris into a storage compartment adjacent the rasp or forward, out of the body.

The profile is optionally symmetric relative to the axis. However, in some embodiments, an asymmetrical profile may be used, for example to better anatomically fit the triangular cross-section of the spinal channel. Alternatively or additionally to axial or trans-axial profile variations, the profile may vary in that its thickness varies along the length of the rasp. In some embodiments of the invention, the variations in profile are effected by the rasp having ribs or a thread.

Figure 4C:
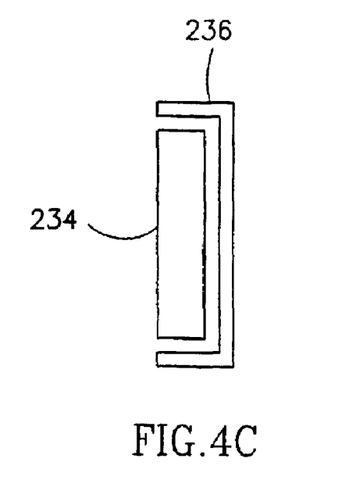

FIG. 4C illustrates an exemplary embodiment of the invention, in which embodiment a shield 236 is used in conjunction with rasp 234 to prevent the rasp from damaging the spinal cord and/or root nerves. Possibly, the shield also serves as a channel for guiding the motion of the rasp. In some embodiments of the invention, the shield is curved, thus guiding the rasp along a curved path. The shield may be relatively rigid or it may be flexible like the rasp itself. In some cases, the shield is formed on the back of the rasp, for example as a smooth surface. In an exemplary embodiment of the invention, the shield does not move with the rasp. Alternatively, both move, but possibly at different rather than same speed and/or direction.

In an exemplary embodiment of the invention, the shield is inserted before the rasp. Alternatively, they are both inserted at the same time. Alternatively, the shield is inserted after the rasp, for example being guided along it. Possibly, a lumen of a catheter or an endoscope is used to guide the shield into the body. Alternatively to being advanced along the channel, the shield (and the rasp, if inserted separately from catheter 226) may be retracted along the channel. In some embodiments of the invention, especially where the shield is curved, the shield may be formed of an elastic, super-elastic or shape-memory material, so that it can be inserted in one shape and then it changes to a different shape.

Figure 4D:
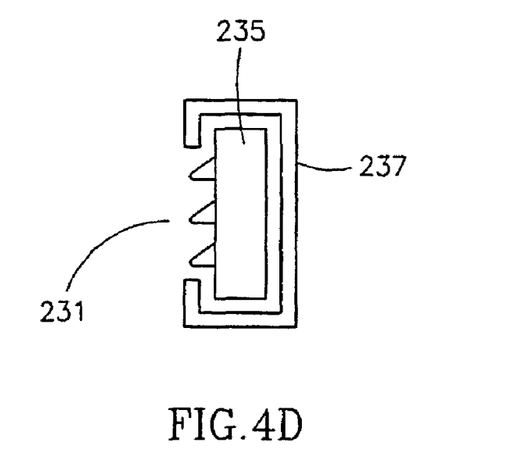

In an exemplary embodiment of the invention, the shield serves to collect debris generated by the rasp and prevent the debris from entering the spinal channel. Possibly, the shield encloses the rasp from more than three sides. FIG. 4D shows such a rasp profile, in which a rasp portion 235 is surrounded by a shield 237 from substantially all sides except for a window 231.

Figure 4E:
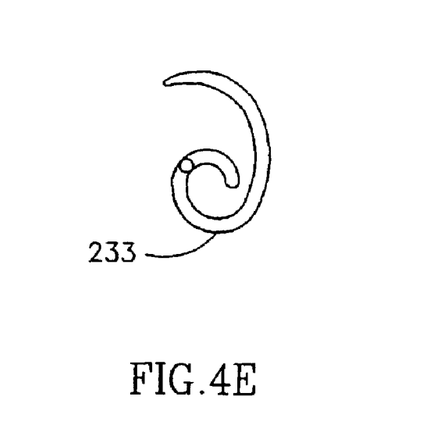

FIG. 4E illustrates a rasp profile 233 including a storage compartment for debris, in accordance with an exemplary embodiment of the invention. In the embodiment shown, a spiral profile is provided, such that when it is rotated counter-clock wise, portions of tissue removed by the leading edge thereof are forced deeper into the spiral.

FIGS. 5A–5E illustrate various types of rasping surfaces, in accordance with exemplary embodiments of the invention. Different types of rasping effects can be produced by selecting different types of rasping surfaces. Some examples of rasping effects desirable in some exemplary embodiments of the invention include sanding, crumbling of bone and removing of bone sections by cutting. The different rasping effects can be achieved, for example by selecting a suitable rasp element profile, by controlling the pressure between the rasp and the bone, by controlling the forward speed of the rasp and/or the power profile in general and/or by adding various fluids, such as air or liquid, during the rasping process.

As can be seen from the exemplary rasp elements shown in these figures, each element has certain structural features, including one or more of an axial, transaxial and top profiles, size, cutting edge and storage for debris. Additionally, various mechanical properties may be set, for example, hardness, sharpness of edge, wear resistance and flexibility. These parameters (and others) may be varied to achieve different types of effects on bone and soft tissue. Additionally, the individual rasp elements may be arranged in different spatial (axial and transaxial) configurations and distributions.

Figure 5A:
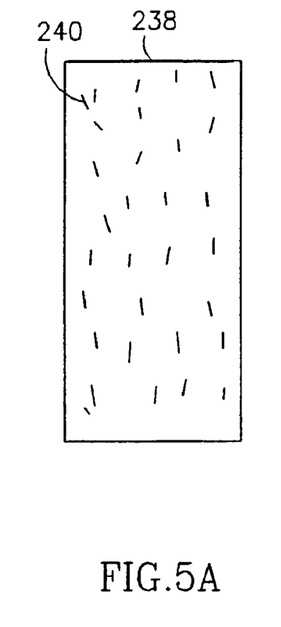
FIGS. 5A–5E illustrate various types of rasping surfaces, in accordance with exemplary embodiments of the invention.

In FIG. 5A, a rasp section 238 has an abrasive surface formed, for example by sandblasting or etching a smooth surface or by attaching a plurality of small protrusions 240 thereto.

Figures 5B, 5C:
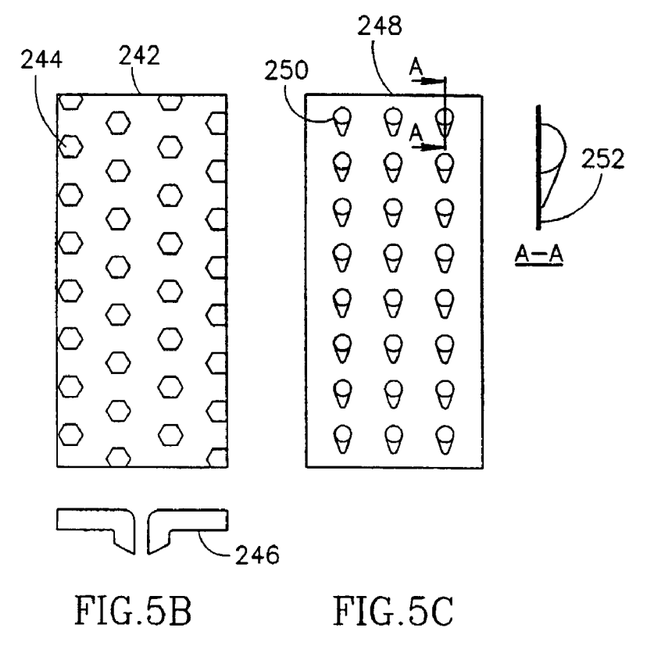

In FIG. 5B, a rasp section 242 has a plurality of hollow rasp elements 244 formed therein, for example by punching. As shown by a reference 246, a side cut-through view of the rasp, the rasp element is cored so that debris caused by the rasping can pass through the rasp. Alternatively to punching, rasping elements 244 may be formed using other manufacturing methods known in the art including, for example, CNC, casting and cold working. In an exemplary embodiment of the invention, the rasp elements are chemically etched from the rasp, to comprise a tab surrounded on three sides by open space. Optionally the tab cutting edge is etched to have a scalloped profile. The distance between the front edge of the tab and the rest of the rasp may be used, in some embodiments, to define the size of bone chip removed by the device. In some embodiments of the invention, the generated chips are used for bone replacement, for example cage surgery for the spine. In an exemplary embodiment of the invention, the chips are removed from a non-vertebral bone. The rasp may be adapted to grate the bone, or to remove thin chips, for example, 0.1, 0.5 or even 1 mm. The rasp surface, aside from the rasp elements may be, for example smooth. In other embodiments, the rasp surface is rough.

In another particular example, a thin layer having rasping elements formed therein is attached, for example using spot welding, to a rasp backing layer, to form the final rasp. Each of these two layers may be formed of a different material.

In FIG. 5C, a rasp section 248 has a plurality of rasp elements 250 attached thereto, formed, for example, by soldering. As shown by a reference 52, a side cut through view, the rasp has different forward and backwards profiles which translate as different amounts resistance to the different motion directions. Alternatively to soldering, rasping elements may be attached to rasp 202 in a variety of ways, including spot welding, gluing, applying pressure or any other method of attaching an element to a surface known in the art. The rasping elements may be formed of a same or a different material as rasp section 248.

Figure 5D:
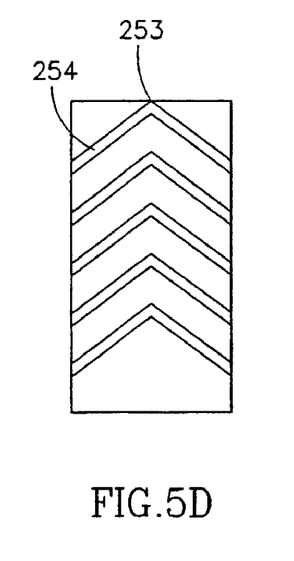

In FIG. 5D, a plurality of rasp elements 254 are aligned to describe V shapes on a rasp section 253. Alternatively, each of the "V"s is formed of a single tissue removal element. A possible advantage of the "V" shape is that the rasp may be less likely to move sideways while in action. Alternatively to a "V" shape, a "W" shape or a wave shape may be provided. Alternatively or additionally, sets of rasps, having different orientations may be used.

Figure 5E:
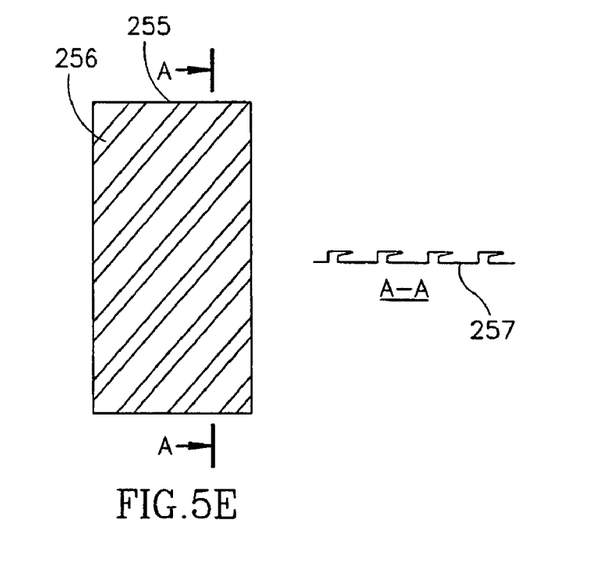

In FIG. 5E, rasp elements 256 are arranged to be slanting to one side on a rasp 255. A profile of the rasp is shown as reference 257. Transaxial movement of such a rasp may be avoided, for example, by properly shaping individual rasp elements which form the slanting elements or by rigid grasping of the elbows 204.

Alternatively or additionally, to formed rasp elements, rasp 255 (for example) may comprise a chain, a cable or a single wire. Possibly, a second wire is spirally mounted on the first wire, to present a rasping surface. In an alternative embodiment, the rasp is a saw with suitably small teeth.

The various properties of the rasping element, as well as their spatial distribution, relative size and orientation may vary axially and/or trans-axially along the rasp, for example as explained above with respect to rasp profile.

In an exemplary embodiment of the invention, the rasp is straight. However, in some exemplary embodiments of the invention, the rasp is curved, for example trans-axially parallel to the plane of device 200 or trans-axially perpendicular to the plane of device 200. This curving may be achieved, for example using a suitably shaped shield 236. This can be achieved in various ways, for example, the shield may be pre-shaped (e.g., shape memory), may be shaped by the insertion process (the elbows) or may be distortable, for example being inflatable or including pull-wires and/or selective weakening so that when force is applied the shield distorts in a desirable manner. Alternatively or additionally, rasp 202 (or the shield layer) may have a suitable resting condition, for example being a shape memory material, a super elastic material or an elastic material, at least having these properties in the direction of the bend. A single bend may be utilized or the rasp can be substantially freeform with any number of bends defined therein. In an exemplary embodiment of the invention, the bends in the rasp are used to make the rasp conform to a particular inner geometry of the spinal column, for example if the vertebra are not properly aligned, or for conditions of bent backs.

In an exemplary embodiment of the invention, device 200 includes a pathway for inserting an endoscopic viewer into the spinal column to view the location of the rasp and its effect on the bone. Optionally, the endoscope is inserted while the rasp is inside the body. Alternatively, the rasp is first removed, possibly leaving a guide wire in the body for easy reinsertion of the rasp, if required.

Alternatively or additionally, device 200 includes a pathway or a lumen for providing vacuum and/or positive pressure (e.g., for irrigation) into the spinal column, for example to aid in removing debris caused by the rasping or to aid in separating the various tissues.

Figures 6A, 6B:
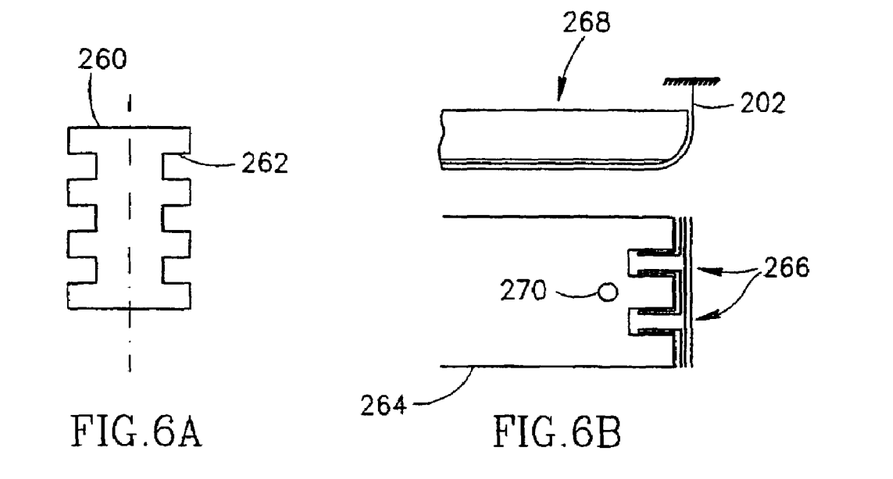
FIGS. 6A and 6B illustrate details of elbows of the device of FIG. 2, in accordance with exemplary embodiments of the invention.

FIGS. 6A and 6B illustrate details of elbows 204 (FIG. 2) in accordance with exemplary embodiments of the invention. In FIG. 6A, a rotating elbow element 260 is shown in which one or more grooves 262 are formed to accommodate rasping elements. These rasping elements are optionally arranged in rows to facilitate their matching such grooves. In FIG. 6B a fixed slip-element 268 is shown, across which element rasp 202 slips. In a side view shown as 264 a plurality of grooves 266 are shown to receive rows of rasping elements. It is noted that in an exemplary embodiment of the invention, elbows 204 can serve to protect the entry and exit point in the spinal column from undue abrasion.

An optional lumen 270 is shown; such a lumen may be used, for example, for the provision of an endoscopic viewer, a vacuum (for debris removal) or irrigation (for debris removal, cooling and/or friction reduction ) into the spinal channel. In some cases, lumen 270 may be at the side of the rasp instead of between the rasp and the bone, as shown. Alternatively or additionally, the lumen may be formed in the rasp or in the shield.

The insertion of device 200, as well as the process of rasping may be performed using any one of the known imaging methods, including, CT, MRI, X-ray, fluorography, angiography, ultrasound and vision (optionally using an endoscope). Possibly, two imaging modalities may be combined or different modalities used for different parts of the procedure, for example x-ray for inserting the rasp and an endoscope for monitoring the rasping process. In an exemplary embodiment of the invention, ultrasound is used to estimate the thickness of the bone, at the point where bone is removed. Various imaging modes can be used, including regular imaging, calculation of velocity in the bone (which velocity is affected by thickness), attenuation measurement and distance measurement (optionally from a fixed position in the spine). In one embodiment the ultrasound is applied from inside the body, from inside the spinal channel. Alternatively, the ultrasound is applied from outside the body. Possibly, an ultrasound transducer used for measurement, is integral with the protector or the rasp.

There are several types of intra-body navigation that can be considered in a context of a rasping procedure as described herein:

(a) navigation of catheter 226 into an out of the spinal column, at the correct locations and without damaging the spinal cord;

(b) navigation of catheter 226 along the spinal channel, avoiding twisting around the spinal cord and damaging branching nerves and/or blood vessels; and (c) trans-axial navigation of the rasp for removing different parts of the cross-section of the lumen of the spinal channel.

Figure 7:
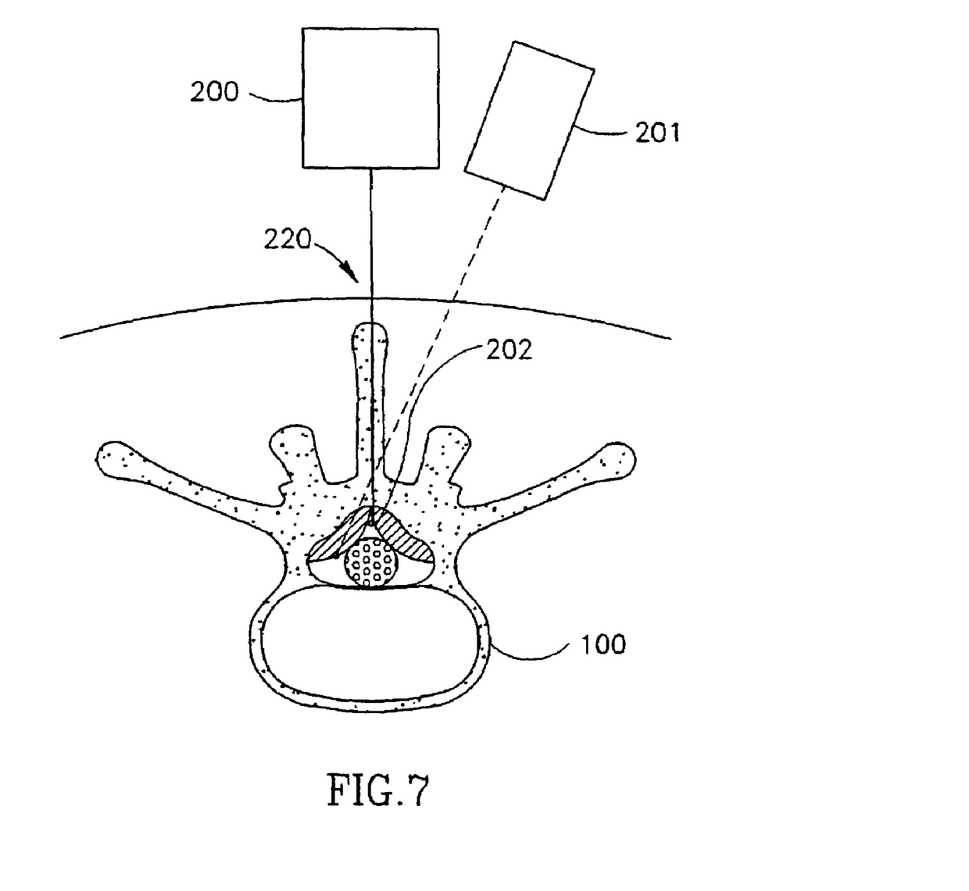
FIG. 7 illustrates trans-axial navigation of a rasp by pivoting the device of FIG. 2 on the body, in accordance with an exemplary embodiment of the invention.

FIG. 7 illustrates trans-axial navigation of rasp 202 by pivoting device 200 around incisions 220 and 228. When device 200 is moved to one side of the spinal midline (as shown by a dotted element 201), the body tissue serves as a pivot which causes the rasp to move to the other side of the spinal midline. The extent of this effect depends, inter alia, on the type of incision (wide, narrow), whether there is a sheath in the incision (e.g., an endoscope) and on the distance of device 200 from the spinal column. Alternatively, this pivoting is provided by a suitably shaped elbow 204. In one example, the elbow is fixed relative to the spine, however it supports sliding of rasp 202 in a trans-axial direction or rotates axially (around the spine axis), so that rasp 202 moves in a trans-axial direction.

One advantage of elbows 204 being fixed relative to the spine is that it confers stability on the location of the rasp in the body, in spite of the considerable and varying pressures exerted on the rasp in various directions.

One issue to be considered in the removal of waste material. It should be noted that the type and size of the particles of the debris depend on the type of rasp elements and the power profile of the rasping activity. In addition, the type, age and disease state of the tissue may also affect the particle sizes. These parameters are optionally matched to the debris removing method selected.

In an exemplary embodiment of the invention, the debris is collected in rasp 202 itself, for example in the hollows of the rasping elements themselves or in a container formed inside rasp 202. The amount or required collections pace depends, inter alia, on the number of times a single element will come in contact with bone and on the amount of bone it removes each time.

Alternatively, the debris is collected between the rasp and the shield layer or in a container formed in the shield layer.

The collected debris may be removed by the forward movement of the rasp, as it advances out of the body. Alternatively or additionally, the debris may be removed by the rasp effecting a spiral motion which pumps the debris out of the body (possibly even uncollected debris). Alternatively or additionally, the debris may be flushed out or sucked out by suitable providing positive or negative pressure at the entry and exit holes or along the rasp. Alternatively or additionally, the container is periodically removed for cleaning.

Another issue to be considered is the provision of a desired pressure between the rasp surface and the bone to be removed. In an exemplary embodiment of the invention illustrated in FIG. 8A, a constant pressure is maintained by fixing device 200 to the spine and providing a spring between the device and the rasp, to control the pressure.

The above description has focused on removing bone. However, it should be noted that in many cases ligament 110 is removed instead of or in addition to bone. The selective removal of one tissue type may be affected in some exemplary embodiments of the invention, for example, by suitably selecting the rasping elements, the rasp profile, rasp placement, rasp-tissue pressure, rasp speed and/or power application profile, In should be noted that in some cases the ligament is removed first, before reaching the bone. In some applications, the rasp may be inserted between the ligament and the bone, to selectively remove the bone without removing the ligament or removing only the bone-facing portion thereof and not the spinal cord facing portion thereof.

Another issue to be considered in some exemplary embodiments of the invention is the provision of feedback of the rasping process, to assess its progress and/or to prevent damage to sensitive tissues.

A basic form of feedback uses one of the imaging modalities mentioned above, or any other modality, to directly image the desired parameter, e.g., the rasp location, amount of bone removed, damage to the spinal cord, etc. Alternatively or additionally, a mechanical measurement method, such as a caliper, may be used.

Alternatively or additionally, other methods of feedback may be used. In one exemplary embodiment of the invention, the thickness of tissue removed is estimated base on parameters of the rasping, for example, the length of time for which the rasp was activated, the pressure applied between the rasp and the tissue, the length the rasp has advanced, the tissue type and/or the amount of tissue removed. Alternatively or additionally, a trans axial motion of the rasp can be measured, using the device of FIG. 8A (e.g., spring 334).

Alternatively or additionally, a color based method can be used. In one variation of this method note is made of the color of removed tissue, and based on the ratio between bone and ligament in the removed tissue, of the thickness of tissue removed, is estimated. Alternatively or additionally, the amount of blood flow is used to estimate the type of tissue being removed. In another variation, the tissue to be removed is stained, over its surface and possibly to a desired depth and note is made of the color of removed tissue. The tissue may be stained, for example, by a first length part of the rasp or by an endoscope or catheter 226 used for this purpose. Alternatively or additionally, to checking the color of removed tissue, a monitoring of the color of remaining tissue may be used, for example using an endoscope or possibly even using a frequency selective photo-sensor mounted inside the body, for example, on one of the elbows or on the shield.

Referring back to FIG. 2, it is noted that the stenosis causing artifacts are often localized. Thus, once the tissue at these areas is removed, a change in the resistance characteristics of the tissue can be expected and/or monitored for. It is expected that bone, ligaments and blood vessel tissue all exhibit different type of resistance profiles to motion of a rasp. In any case, if the rasp engages more than a certain percentage of the spinal column a safety hazard can be decided and the operation stopped automatically.

In a related method, it is noted that once these stenosis causing locations are treated, the displacement of the rasp will change significantly. The amount of displacement or the rate of change of displacement may also be used to estimate the thickness of tissue removed.

In another method, the amount of tension in the rasp is monitored. In an exemplary embodiment of the invention, when a sudden change in tension is detected a break in the rasp is determined, and the power stopped. Alternatively or additionally, if the amount of tension at either end of the rasp is significantly different from the other end, a determination that the rasp is stuck may be made.

In another method, the operation is stopped periodically so that a doctor can obtain tactile or audio feedback, for example by moving the rasp manually.

In another method, the rasp elements are degraded as they are used, once a certain part of the rasp has removed a certain amount of bone, all the rasp elements at that part are smoothed and that rasp portion does not cause any more tissue removal. Alternatively or additionally, the rasp may include a portion which is degraded as the rasp is used, and the thickness and/or opacity of that portion examined to assess the amount of tissue removed.

In some exemplary embodiments of the invention, safety mechanisms are provided to avoid nerve damage. In an exemplary embodiment of the invention, measurements of evoked potential are carried out on the branching nerves, to determine changes in pressure caused by the spinal stenosis. Alternatively or additionally, conduction velocity in the nerves may be measured to monitor the reduction in stenosis and/or damage caused by the treatment. In an exemplary embodiment of the invention, prior to measurement the rasp is rotated around the axis of the spine to a location where there is more room, so that the rasp itself does not exert pressure on the spine. Alternatively or additionally, the rasp includes a pressure sensor at its back and/or the back of the shield, so that the contact pressure between the rasp an the spinal cord can be monitored.

Figure 8A:
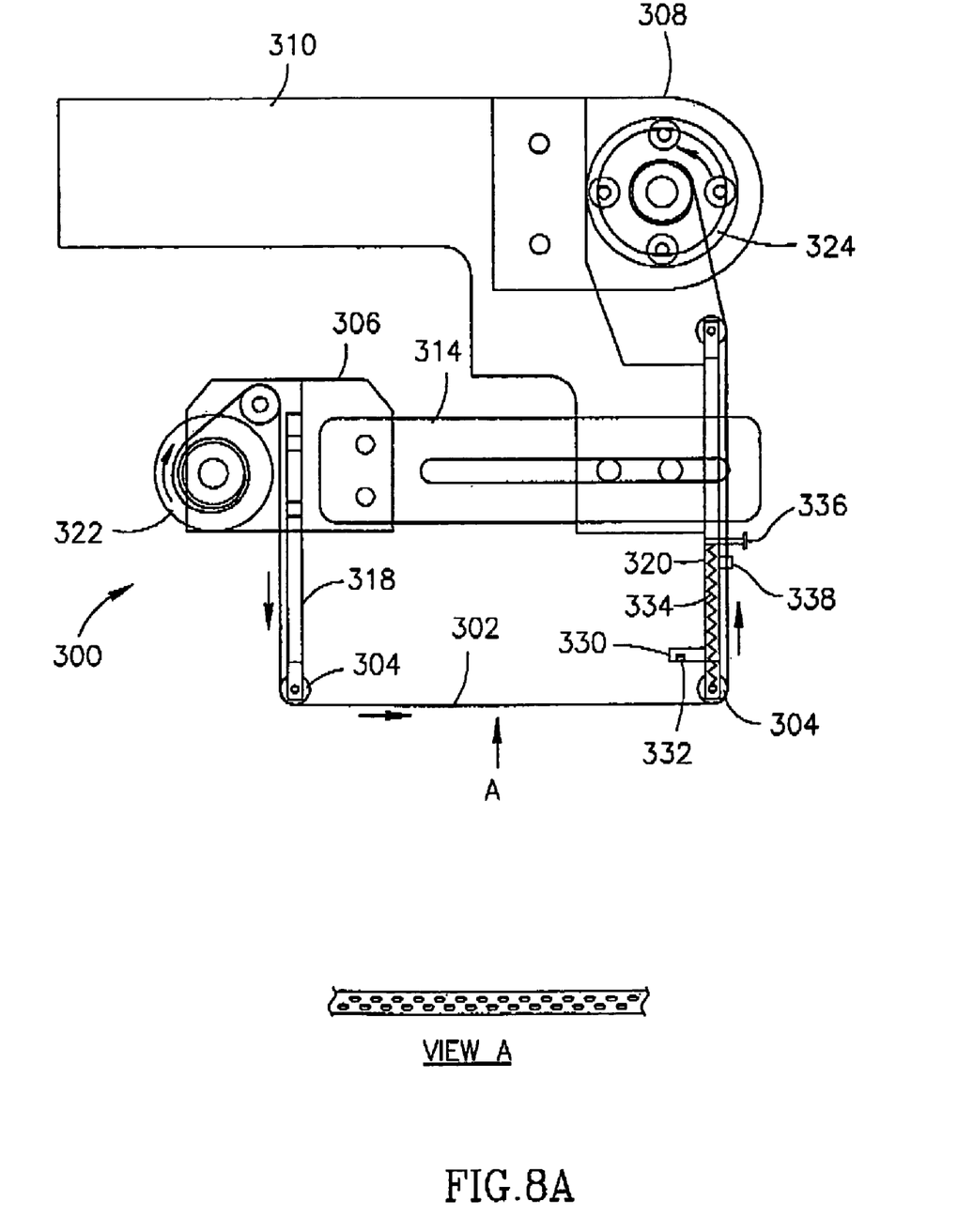
FIG. 8A is a side view of a detailed embodiment of a bone removal device, similar to the device of FIG. 2, in accordance with an exemplary embodiment of the invention.
Figure 8B:
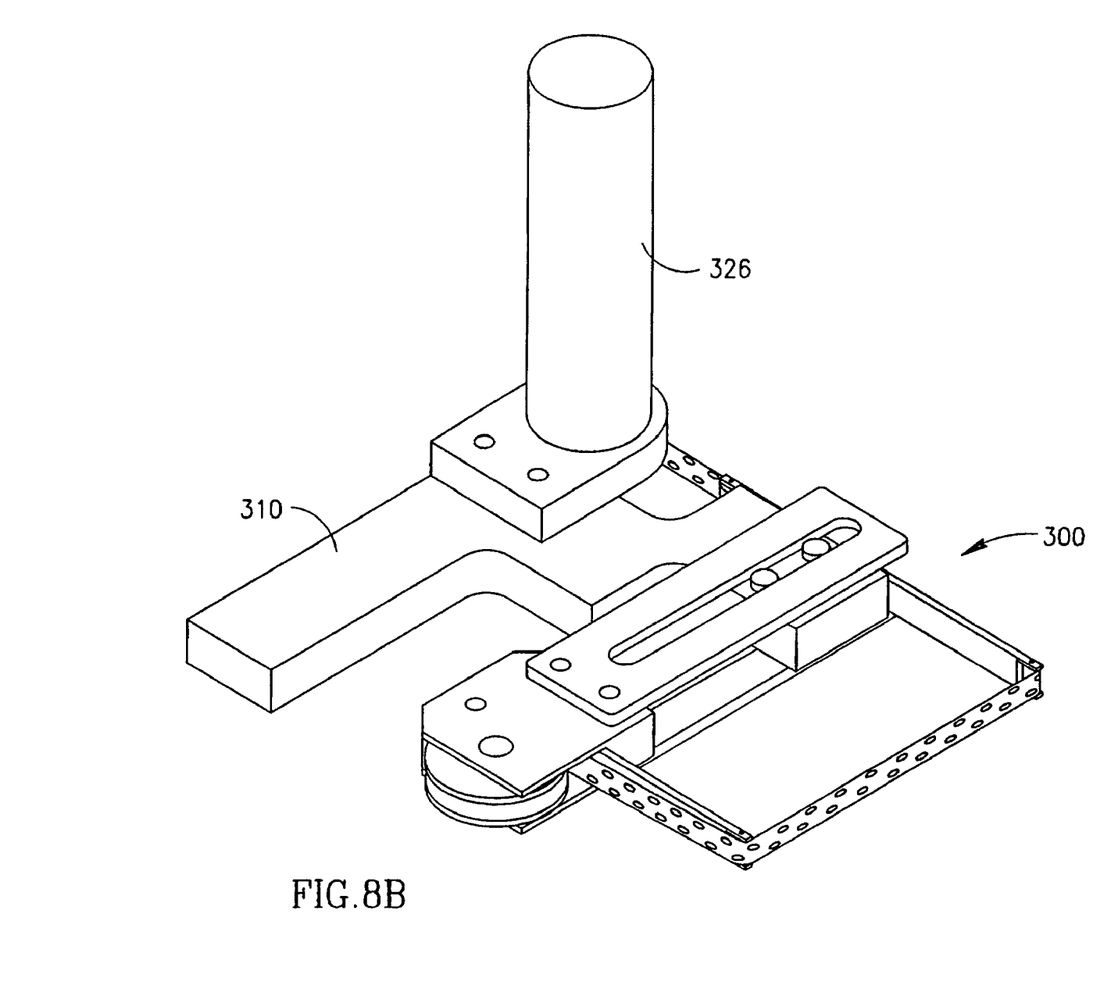
FIG. 8B is an isometric view of the device of FIG. 8A.

FIG. 8A is a side view of a detailed embodiment of bone removal device 300, similar to device 200, in accordance with an exemplary embodiment of the invention. FIG. 8B is an isometric view of device 300, omitting some elements. Device 300 comprises a rasp providing unit 306 which provides a rasp 302 from a rasp reel 322, along an inserting extension 318 to a first elbow 304 and then to a removal elbow 304', along a removal extension 320 and to a rasp uptake reel 324 which forms part of a rasp take up unit 308. Providing unit 306 and take-up unit 308 are optionally interconnected using connector 314, which can control the distance between the take-up and the providing units. This distance can be used to directly control the length of spinal column treated or, if extensions 318 and/or 320 can be angled, as in some exemplary embodiments of the invention, to indirectly control this length.

A handle 310 and possibly a perpendicular handle 326 are provided to allow a physician to hold the device in a stable manner. Alternatively, device 300 may be fixed relative to the patient and/or a patient bed.

In an exemplary embodiment of the invention, a bone rest 330 is provided, so that device 300 can rest directly against the bone. Alternatively or additionally, a back rest is provided so the device rests against the skin of the back of the patient. In an exemplary embodiment of the invention, bone rest 330 expands radially, so that it can be easily inserted into a narrow incision. Alternatively other solutions may be provided, for example the bone rest may fold or a larger incision used. In an exemplary embodiment of the invention, bone rest 330 includes retractable spikes (not shown) for engaging the vertebra). Alternatively or additionally, bone rest 330 matches the anatomy of the vertebra to assist in achieving a stable resting configuration.

In an exemplary embodiment of the invention, elbows 304 are attached to device 300 using a spring 334, which controls the pressure exerted by rasp 302 against the spinal column. In an exemplary embodiment of the invention, a screw or other element 336 is provided for controlling the tension in the spring. Optionally, when the device is inserted a low or null tension is provided and once the bone rests are in place, the, spring is activated. Possibly, a sensor 332 is provided to determine proper contact between bone rest 330 and the spine. Possibly, device 300 is inactivated if a low and/or high contact pressure is detected. Alternatively or additionally, a sensor 338 is provided to measure the tension in the spiring and/or to measure displacement of elbow 304 relative to bone rest 330. In an exemplary embodiment of the invention, two such bone rests are used, even though only one is shown. In other embodiments, only one bone rest is used.

In an exemplary embodiment of the invention, catheter 226 is threaded on take-up reel 324 after it passes through the spinal channel. Alternatively rasp 302 is directly threaded on the take up reel.

In an exemplary device, rasp 302 is 5 meters long, 4 millimeters wide and between 0.05 and 0.15 millimeters thick. The motion is reciprocating at an amplitude of 2 millimeters and a frequency of 1 Hz and the rasp advances at a speed of 1 meter a minute. In this example, the AC motion magnitude is significantly greater than that of the DC motion. In other embodiments, the magnitudes may be similar or the DC motion may be smaller.

In an exemplary embodiment of the invention, the rasp material is metallic, for example stainless steel. Alternatively or additionally, at least the rasp elements are formed of plastic. One advantage of plastic is that it can be made bio-absorbable so that any pieces which chip off are rapidly absorbed and do not cause mechanical damage or promote infection. Alternatively or additionally, the rasp is formed of a cloth material, possibly with abrasive material glued on. One possible advantage of cloth is an increased resistance to tearing and/or other types of mechanical failure.

In an exemplary embodiment of the invention, parts of device 300 are made for a single use and/or for a single patient. In one exemplary embodiment, the entire device is a one-time device. In another exemplary embodiment only rasp 302 is one time and is provided, for example packaged with a providing reel 322 or with an entire providing unit 306. In another exemplary embodiment, all the portions which come in contact with body fluids are disposable and/or separable and sterilizable, possibly being provided as a cartridge which encompasses the rasp, the extensions, the elbows and optionally the reels.

As can be seen in FIG. 2, not all the tissue along the spinal channel needs to be abraded. Optionally, only the protrusions are abraded. In many cases, the less tissue area is treated the better. First, the stability and mechanical strength of the spine are in less danger of being compromised. Additionally, there is usually a smaller danger of infection. Third, any removed tissue locations may be a danger to the spinal column, either by having sharp edges or by overcompensated healing growth.

A first type of selectivity is selecting which tissue type to removed, for example only bone or only ligament. This selectivity may be achieved, for example by suitable controlling of the rasp structural and/or movement parameters. Another method of achieving this selectivity is to provide a rasp having two parts, a ligament removal length and a bone removal length and to selectively use the desired part (or separate devices). Possibly, two or more rasp types may be threaded simultaneously through the spinal channel and only one used at a time. In another variation, the rasp is two sided, with each side having a different effect on tissue.

Alternatively or additionally, a local axial variation method may be used, in which method nearby portions of the rasp have different tissue effects. In an exemplary embodiment where the rasp is rotated, only those portions which have a bone removing effect will remove bone while nearby portions will not. In an exemplary embodiment where a rasp is axially advanced. The amplitude of reciprocating motion is kept small and once that part of the rasp is done rasping, the rasp is advanced a great amount, so that it does not removed undesired bone. In some embodiments, the rasp is neutral with regard to tissue abrasion and a tissue affecting element is advanced along the rasp to a desired abrasion location.

Alternatively or additionally, portions of the rasp may be prevented from performing their abrasive function, for example by sliding one or more shield segments over the rasp so that only at desired windows is the rasp in contact with body tissue. Alternatively or additionally, these shield segments may affect the distance between the rasp and the body tissue, the tension, the pressure and/or rotate the rasp. In an exemplary embodiment of the invention, the shield provides the tension in the rasp, for example by applying transaxial pressure against the rasp.

Alternatively or additionally, by matching a controlling of the rasp motion parameters, such as stroke length, tension, frequency, etc. with the local rasp structure, various rasping effects can be achieved.

In an exemplary embodiment of the invention, especially when selective rasping is performed, an image guided procedure is used in which the position of the rasp relative to the tissue to be removed is shown. The image is optionally coupled to the rasp device, possibly simplifying coordinate registration problems however, this is not required. The rasp optionally includes markers which enable the axial position of the rasp to be determined from the image, however, this is not required.

Alternatively or additionally, the position of the rasp is determined using an optical encoder or a different type of encoder on the rasp or on one or both of the reels.

In an exemplary embodiment of the invention, the rasp position determination is utilized by a controller to match desired variations in rasp structure and/or rasp movement to a particular situation. Optionally, an image or scheme of the spine showing what is to be removed in first entered into the computer, to plan the procedure, however, this may also be done in real time. Alternatively or additionally, to computer control, manual "fast forward", "reverse" and "activate" buttons may be provided, as well as controls to vary selected ones of the myriad of available parameters.

The rasping process itself may proceed as a single extended step in which a single type of activity is performed until the desired rasping effect is achieved. Alternatively, a multi-step process may be used, for example first rough rasping and then fine rasping or rasping one vertebra at a time (even though all the vertebra are threaded by the rasp) or first removing ligament and then removing bone.

Alternatively or additionally, once the rasping is completed, the availability of the rasp threaded in the body may be used to treat the rasped area, for example using radioactivity or heat (to prevent re-growth) or by applying pharmaceuticals, such as healing promoters. These materials may be attached to the rasp itself or may be guided along or over the rasp and/or the shield, for example using one or more catheters or endoscopes.

In an exemplary embodiment of the invention, the rasp is cooled (inside the body) or pre-cooled (prior to being inserted into the body. This cooling can be used to counteract the friction heating of the rasp. Alternatively or additionally, the cooling can be used to affect the tissue structure and assist in tissue removal and/or in the selectivity of tissue removal. Thus, the cooling may be towards the bone or towards the nerve. Possibly the rasp include a material with a high thermal coefficient, so that the cooling effect is maintained. Alternatively or additionally, the rasp or the shield include insulation, to block the heat from reaching the spinal cord. Alternatively or additionally, to cooling, heating may be applied, for example to counteract excessive cooling. Possibly, the motion of the rasp is made responsive to its temperature, which may be measured in the body or after it leaves the body. Alternatively or additionally, a cooling liquid is provided in the spine. The temperature of this liquid may be monitored to prevent adverse effects of heating.

In some exemplary embodiments of the invention, a support mesh or another type of membrane is provided over the rasped area, for example to promote healing or to prevent adhesion.

In an exemplary embodiment of the invention, the power for moving the rasp is provided at the take-up reel. Possibly, the power is electric, pneumatic or hydraulic. Alternatively or additionally, the power is manual, being apply by a physician, for example, either by turning the reel or by advancing the entire device 300. Alternatively or additionally, power may be provided at least partly locally, for example by providing piezoelectric materials on the rasp, which when activated, cause the rasp elements to move. Alteratively or additionally, vibration of the rasp may be affected by providing a rasp with a high Q factor, for efficient transmission of ultrasonic vibrations along the rasp, from outside the body.

In an exemplary embodiment of the invention, the power train includes various safety featured. In one example, a clutch is provided which only releases the rasp to move if a minimum amount of rasp-bone pressure is applied or if a minimum amount of tension is achieved in the rasp. Another example is a maximum power cut-off that stops the rasp motion if the required power is above a pre-selected limit or a calculated limit.

Alternatively or additionally, to remove portions of the spine for treating spinal stenosis, portions of the spine may be removed for other reasons. One possible application is removing portions of the spine to aid in straightening a bent back. By allowing controlled removal of bone without major surgical incisions, less aggressive treatments than practiced today may become more prevalent. Alternatively or additionally, portions of the bone on the outside of the spine may also be removed and/or grooves formed therein, for example to assist in bending of the spine.

Alternatively or additionally, a similar device may be used for removing bone portions from outside the spine. Instead of the rasp pointing towards the device, the rasp (and/or a shield thereof) can be twisted 90° or 180° around its axis so that it points away from the device. Such a modified device can still be used without a major incision. Alteratively or additionally, such a device may be used for forming groves (straight or curved ) in other bones, such as a femur. When forming such a groove, a two step process may be used. In a first step a deep narrow grove is formed and the rasp inserted therein. In a second step, the rasp is rotated or expanded (or a wider rasp provided) so that a wider diameter groove is formed at the base of the narrow groove.

Alternatively or additionally, minimally invasive removal of bone may be practiced. For example to aid in straightening bent bones (e.g., a femur), for applying bone plates to broken bones, with a better conformity to the bone geometry (possibly along the path of the rasp) and/or for corrective surgery of deformed complex joints, such as wrists and ankles, where a plurality of bones need to be reshaped to match against each other. In some of these applications it may be useful to provide a bone drill and/or a rotary rasp, alternatively or additionally to a liner rasp. In an exemplary embodiment of the invention, the rasp is deployed inside an intra-medullar space of a bone with the rasp pointed in the direction of the device, to the side or even away from it.

In an exemplary embodiment of the invention, a portion of vertebral bone may be removed with a minimal compromising of the surface of the vertebrae, inside the spinal channel and/or outside of it. A bore may be drilled in the vertebra, from between two vertebrae along a path which does not intersect with the surface of the vertebra. The removal of the bone softens the vertebra, so that inflating a device inside the spinal channel and/or otherwise applying pressure against the vertebra from inside will increase the radius of the spinal channel. Alternatively, after the bone bore is removed, the inside of the bore is hooked and retracted, to cause it to collapse, Thus, there may be less danger of inflammation adjacent the spinal column. In an exemplary embodiment of the invention, the tool used for boring comprises a drill and/or a rasp.

In the above description, an entry-exit device has been described. However, in some exemplary embodiments of the invention a single hole device is used, which is inserted into the spine as in FIGS. 3A and 3B and then activated, without requiring the rasp to exit the body as in FIG. 3C. In one example an extension 318 can be extended into the spinal channel and the rasp run along it. One type of suitable rasp is a self-engaging rasp, in which the rasp elements, once in contact with the bone, engage the bone to a greater extent, reducing the need to apply external pressure to maintain proper contact between the rasp and the bone. In addition, higher motion frequencies may be used. One suitable type of rasp motion is reciprocating. Possibly, the rasp is arranged like a conveyor belt, so that used parts of the rasp exit along the same path that they used to enter the body, optionally separated from the spinal cord by a shield layer. Alternatively or additionally, rotational motion of the rasp may be used for removing bone.

Such a one-sided device may be especially useful for treating stenosis of the branching nerve channels. In an exemplary embodiment of the invention, a rigid shield is provided to protect the branching nerve. Possibly, the shield has a form adapted to the anatomy of the channel. The rasp is optionally a rotational rasping device.

It will be appreciated that the above described methods of removing spinal blockages and the various apparatus described may be varied in many ways. In addition, a multiplicity of various features, both of methods and of devices have been described. It should be appreciated that different features may be combined in different ways. In particular, not all the features shown above in a particular embodiment are necessary in every similar exemplary embodiment of the invention. Further, combinations of the above features are also considered to be within the scope of some exemplary embodiments of the invention. Also within the scope of the invention are surgical kits that includes sets of medical devices suitable for reliving a stenosis and/or performing other parts of a surgical procedure. When used in the following claims, the terms "comprises", "includes", "have" and their conjugates mean "including but not limited to".

It will be appreciated by a person skilled in the art that the present invention is not limited by what has thus far been described. Rather, the scope of the present invention is limited only by the following claims.

The invention claimed is:

1. Apparatus configured for entering the spine of a body of a live human patient through separate first and second incisions, made in the patient adjacent to different vertebrae in the spine, to remove material from the spine, the apparatus comprising:
   a handle;
   first and second elongate extensions, attached to said handle, long enough to extend, simultaneously, from the handle respectively through the first and second incisions to separate first and second locations along the length of the spine; and
   a flexible rasp configured to pass along the first extension into the body through the first incision and up to the first location on the spine, through a spinal channel from the first location to the second location, and from the second location along the second extension out of the body through the second incision.

2. Apparatus for removing bone, comprising:
   a handle;
   a first extension attached to said handle;
   a second extension attached to said handle;
   a flexible rasp adapted for passage through a spinal channel of a live human, extending between a tip of said first extension and a tip of said second extension; and
   means for affixing said apparatus to a vertebra.

3. Apparatus according to claim 2, wherein said rasp moves axially between said tips.

4. Apparatus according to claim 3, comprising a take-up reel for advancing said rasp between said tips.

5. Apparatus according to claim 2, comprising a shield adjacent said rasp, to prevent contact of said rasp with tissue at at least some locations along said rasp.

6. Apparatus according to claim 5, wherein said rasp has two faces, and wherein said shield protects tissue from one face of said rasp.

7. Apparatus according to claim 5, wherein said rasp is positioned between said shield and said handle, such that said rasp has an at least partially unshielded active face towards said handle.

8. Apparatus according to claim 5 wherein the relative positions of the rasp and shield with respect to said handle are changeable by rotation of at least one of the rasp and the shield around an axis connecting said tips.

9. Apparatus according to claim 5 wherein said rasp has two narrow sides and wherein said shield protects tissue from the sides of said rasp.

10. Apparatus according to claim 5 wherein said shield is fixed relative to said tips.

11. Apparatus according to claim 5 wherein said shield is adapted to move axially with said rasp.

12. Apparatus according to claim 11 wherein said shield comprises a smooth backing on said rasp.

13. Apparatus according to claim 10 wherein said shield comprises a channel within which said rasp is positioned.

14. Apparatus according to claim 13 wherein said shield cooperates with said rasp to accumulate tissue removed by said rasp between said rasp and said shield.

15. Apparatus according to claim 2 comprising at least one resting point at at least one of said extensions, which resting point is adapted to engage a vertebra.

16. Apparatus according to claim 2 wherein said rasp has a transaxial width narrow enough to fit inside a vertebral channel of a adult human.

17. Apparatus according to claim 2 wherein said rasp is less than 7 mm wide in a transaxial direction.

18. Apparatus according to claim 17 wherein said rasp is less than 5 mm wide.

19. Apparatus according to claim 18 wherein said rasp is less than 3 mm wide.

20. Apparatus according to claim 19 wherein said rasp is less than 2 mm wide.

21. Apparatus according to claim 20 wherein said rasp is thinner than 1 mm.

22. Apparatus according to claim 21 wherein said rasp is thinner than 0.5 mm.

23. Apparatus according to claim 22 wherein said rasp is thinner than 0.3 mm.

24. Apparatus according to claim 23 wherein said rasp is thinner than 0.1 mm.

25. Apparatus according to claim 2 wherein said rasp is adapted to remove vertebral bone.

26. Apparatus according to claim 2 wherein said rasp is adapted to remove calcifications.

27. Apparatus according to claim 2 wherein said rasp is adapted to remove ligament tissue.

28. Apparatus according to claim 2 wherein said rasp is formed of metal.

29. Apparatus according to claim 2 wherein said rasp is formed of a bioabsorbable material.

30. Apparatus according to claim 2 wherein a plurality of rasp elements are attached to said rasp.

31. Apparatus according to claim 2 comprising a source of cleaning fluid, adjacent said rasp.

32. Apparatus according to claim 2 comprising a source of vacuum, adjacent said rasp.

33. Apparatus according to claim 2 wherein said rasp has a total length selected to be substantially sufficient for a spinal stenosis removal procedure.

34. Apparatus according to claim 2 wherein said rasp has a total length of between 0.5 and 4 meters.

35. Apparatus according to claim 34 wherein said rasp has a total length of between 1 and 3 meters.

36. Apparatus according to claim 2 wherein said rasp has an active length defined by a distance between said tips.

37. Apparatus according to claim 36 wherein said active length is adjustable by adjusting a distance between said tips.

38. Apparatus according to claim 36 wherein said active length is sufficient to span between one and ten vertebra of a adult human.

39. Apparatus according to claim 36 wherein said active length is sufficient to span between two and eight vertebra of a adult human.

40. Apparatus according to claim 36 wherein said active length is sufficient to span between three and four vertebra of a adult human.

41. Apparatus according to claim 2 wherein said extensions are sufficiently long to extend from a body surface to a spinal channel of a adult human.

42. Apparatus according to claim 2 comprising a rasp advancer for advancing said rasp in a single direction.

43. Apparatus according to claim 2 comprising a rasp advancer for reciprocating said rasp.

44. Apparatus according to claim 2 wherein said apparatus comprises at least two parts, separable such that said first and said second extensions are in separate parts during a normal use of said apparatus.

45. Apparatus according to claim 2 comprising a spring for setting a tension in said rasp.

46. Apparatus according to claim 2 comprising a spring for setting a surface pressure of said rasp against a working surface.

47. Apparatus according to claim 2 comprising a gauge for measuring a tension in said rasp.

48. Apparatus according to claim 2 comprising a leader attached to one end of said rasp, which leader is adapted for inserting though a spinal channel.

49. Apparatus for spinal stenosis treatment, comprising:
   means for guiding a rasp through a part of a spinal channel defined by at least one vertebra;
   means for holding said rasp on either side of said part of a channel and outside a human or animal body including said vertebra; and
   means for moving said rasp to remove a spinal stenosis in said spinal channel.

50. A method of treating spinal stenosis in a live human patient with a flexible rasp, the method comprising:
   making a first incision and a second incision in the body of the patient;
   contacting the spine through one of the incisions with a device for guiding the rasp;
   passing the rasp from outside the body, through the first incision to a first location on the spine;
   passing the rasp through the spinal channel from the first location to a second location on the spine;
   passing the rasp out of the spine at the second location, and out of the body through the second incision; and
   moving the rasp in order to remove tissue from the spinal channel;
   wherein at least part of passing the rasp is guided by the rasp guiding device.

51. A method according to claim 50 wherein passing the rasp through the spinal channel comprises passing the rasp along the spinal channel over a length of at least one vertebra.

52. A method according to claim 51 wherein the first and second locations on the spine are distanced by at least two vertebrae.

* * * * *